United States Patent [19]
Webb et al.

[11] Patent Number: 5,827,518
[45] Date of Patent: Oct. 27, 1998

[54] VIRAL AND INSECT GENES THAT INHIBIT THE IMMUNE SYSTEM AND METHODS OF USE THEREOF

[75] Inventors: Bruce Allen Webb; Liwang Cui, both of Lexington, Ky.

[73] Assignee: University of Kentucky Research Foundation, Lexington, Ky.

[21] Appl. No.: 622,354

[22] Filed: Mar. 27, 1996

[51] Int. Cl.$^6$ .............................. A61K 39/12; C12N 15/86
[52] U.S. Cl. ...................................... 424/186.1; 424/199.1; 424/204.1; 424/93.2; 424/93.6; 435/320.1; 536/23.72
[58] Field of Search .............................. 435/69.1, 172.1, 435/320.1, 172.3; 536/23.1, 23.5, 23.7, 23.72; 424/186.1, 199.1, 204.1, 93.2, 93.6

[56] References Cited

PUBLICATIONS

Webb and Luckhart, "Evidence of an Early Immunosuppresive Role for Related *Campoletis Sonorensis* Venom and Ovarian Proteins in *Heliothis Virescens*", Jun. 14, 1993, pp. 147–163, Department of Entomology, New Brunswick, NJ.
Schmidt et al., "Role of Virus–like Particles in Parasitoid–Host Interaction of Insects", Subcell. Biochem., 15:91 (1989), Institute for Biology III, Germany.
Davies et al., "Interference with function of plasmatocytes of *Heliothis Virescens* in vivo by calyx fluid of the parasitoid *Campoletis sonorensis*", 1988, pp. 467–475, Department of Entomology, College Station, Texas.
Hayakawa, "Cellular Immunosuppressive Protein in the Plasma of Parasitized Insect Larvae", May 20, 1994, pp. 14536–14540, The American Society for Biochemistry and Molecular Biology, Inc..

S. Bradleigh Vinson, "How Parasitoids Deal With the Immune System of Their Host: An Overview", Sep. 23, 1989, pp. 3–27, Department of Entomology, College Station, Texas.

Summers et al., "Polydnavirus–facilitated endoparasite protection against host immune defenses", Jan. 1995, pp. 29–36, Department of Entomology, College Station, Texas.

Li et al., "Apparent Functional Role for a Cysteine–Rich Polydnavirus Protein in Suppression of the Insect Cellular Immune Response", Aug. 4, 1994, Department of Entomology, New Brunswick, NJ.

Krell et al., "Virus with a Multipartite Superhielical DNA Genome from the Ichneumonid Parasitoid *Campoletis sonorensis*", May 27, 1982, Department of Entomology, College Station, Texas.

Dib–Hajj et al., "Structure and evolutionary implications of a cysteine–rich *Campoletis sonorensis* polydnavirus gene family", Jan. 26, 1993, Department of Entomology, Texas and New Jersey.

*Primary Examiner*—David Guzo
*Attorney, Agent, or Firm*—McDermott, Will & Emery

[57] ABSTRACT

Viral, endoparasitoid and/or host genes that specifically inhibit the immune response of insect pests, useful for broadening the host range of insect viruses. Symbiont viruses of insect pests are genetically modified to express immune-suppressing proteins or biologically active fragments thereof and, optionally toxins, to increase the virus host range and/or improve the efficacy of insect pathogens.

14 Claims, 8 Drawing Sheets

| | | | | |
|---|---|---|---|---|
| GCTATCGCGA | TACAATTTCC | AGCTAAATTA | TCGTTAGGTC | GTCCGGGTCA | GCTCGAACGA | 60 |
| GAGGCCAGCT | ACTGGGTGCT | TACATGTATA | AAAGCACAGT | CCCGCCCTCA | ACAATCCAGA | 120 |
| GTATTACTTA | TCGCGGCCTG | CGCGTCGGAC | AATTTTTTCA | TTGTAAGTAT | TTCATAAAAA | 180 |
| ATCCAATTTG | TTCGTAGATA | GTTGTGGACT | AATCCTTCTT | CGTAACCGTC | GAATGAAGGA | 240 |
| GCCATTTCAT | AATTAAATAC | AATGTTTTAT | TTGTTACTAT | TCGCAGATAA | TAAATCATAG | 300 |
| CATTACCTGG | ACCATGAAGT | TTTTGTGGTT | TGCACTGGTC | GCAGTGGTTA | CAGTGGCTGC | 360 |
| GCATCCTGTG | GTCGAGACAT | CAACTGAGAA | AGAGGCCGAC | GGGAAAACTT | CGCCCCAATG | 420 |
| CGAGCCAGGG | TGCATCGGCA | ATTACCAACC | TGTAAGTACA | TCATTGCTAG | CACTTTGTCA | 480 |
| ACAAACCATT | GGAGCATATG | CCTGCTGAAA | CTCTTTACCG | ACGAATGTGT | CGTTAGTGAG | 540 |
| ATGATGGAGA | TGTCTACTTT | ATATATTGGA | ATAGAATATC | TATACCTAAC | ATACCATGTC | 600 |
| AAATTCAATT | AAGATAAATAT | TGTCTTGTAT | GTTTCAGTGC | ATTGAGTCGA | CGAAGCCCTG | 660 |
| CTGCCGACTT | GAAGATCGCA | CATCGGTGCA | ATTTGGACGT | AAAGAGTACA | TCTGTGATCG | 720 |
| ATTCTTCGGC | GGACTCTGTG | CCCCATTAGA | CGTCATAAAC | AACCTTACAC | TGTATAAAGA | 780 |
| ATTGAGTGCA | CAATTGAACG | AAACTAATTT | GGCGGAACTC | TCCAATCTGT | ATTTCCAAGG | 840 |
| TATAAAGCAC | ACGCTGGGAA | TCAAGCCAGA | ACCCAAGATA | GAAGACGCGG | GAAAAGTCGA | 900 |
| GGAAGTCGTG | AAACAGAGTA | CGGACAACAT | GAAATTGAGT | ACCGAAGCCG | AACGTGAACC | 960 |

Figure 1a: SEQ ID NO:1:

```
TGGAGACAAG ACAGTATCCG GAACAGAAAA CTGGGTACAA TCCCCAGACA CGGATTCGCC   1020
TATTAACAAC AAACCTGTAA GTACATCATT GTTAGCACTT TGTCAACAAA CCATTGGAGC   1080
ATATGCCTGG CTGAAACTCT TTACCGACGA ATATGTCGTA AGTGAGATGA TGGAGATGCC   1140
TACTTTATAT ATTGGAATAG AATATCTATA TCTAACATAC CATGTCAAAT TCAATTAAGA   1200
TAATATTGTC TTGTATGTTT CAGTGCATTG AGTCGAAGGA GTCCCGCTGC CGACTTGAAA   1260
ATCGCACATT GGTGCAATTT GGACGTGAAG AGGACATCTA TGGTCGATTC CTCGGGCGGA   1320
TCTATGCTCC ATTAATAGTC GTTAACAACT CCACACTGTA TTTAGAATTG AGTAAAGGAA   1380
TGAACGAAAC TAAATTGTCG AATCTCAGCG ATTGGTATAT AGCAGCAGCT GTAATCCCCA   1440
TGCCGGAATT CAAGCCAGAA TCCAAGATAG AAGATGAGCG AAAATCCCCA GAAGCCCCAG   1500
AACTCGAGTC ACAGTGCATC CCAAATTATG AACTGGTAAG TAAATAATGG ATACCACTTC   1560
ATTATTCAAT CGTTCAAGCA TATGACTGAT GGAACTCCCC AACAAAATGT ATGTTTTATG   1620
CCACCACGCT GAAACCCTCC GCGACAGATG CCTTTGACGA TGAACGATTA   1680
CAGCATATAT TGGAATAGGC ATCGTGTACT TTTCCACATG TCACGCCCTT TAACATGTAT   1740
TGAAGTAGAC ATCGTCACGT TTTATCTCTG GGAGAGTCTG TGAGCAATTT CACGGGGTAC   1800
ACTCTTAGTT ATTCTCAATC TGTCGTCGTG GATCTTGTGA ACTTGAACTA CATCAATGTC   1860
ATTTTGTATA TTTTCAGTGC GTGAATTCGA AGAGGCCCGTG TTGCTGGGAG AATAAGCTGT   1920
```

Figure 1b: SEQ ID NO:1:

```
TCGCTGGTTC ATCTAAACCC CGTAATTTCG TATGCGGTCT ACACGGCCGA AGCTACTGTT    1980
CACCATTCGA TGGCTAACCA ATTGGATATT CGCTGGAAGG TCGACAGGTT AAGGGAACAA    2040
GAATCGATCA AGAAGGAAGT TTACGCTGTC GACTTTTCAT CAACAAGGAC CACTTTTTCC    2100
GTTTTTCAAC TGAGCTAGAG GTGGTTCTTG TTTTATACGA ATATTTTTTA ATGTCTTTTG    2160
TGTTGCATTA AGCATTTTTT GAAATTTTGT CTTCCCTTAT ATCAATAATT TTAGGTTGCA    2220
TGTCGTTGAA AAACTATTTA GTTTATTATA AGAAGGAATA ATGTAATATG TTTCAAGATT    2280
TTTTTTCAAT AAAGAGTAAT GATAATTAAA
              2310
```

Figure 1c: SEQ ID NO:1:

```
Met Lys Phe Leu Trp Phe Ala Leu Val Ala Val Val Thr Val Ala Ala
 1               5                  10                  15

His Pro Val Val Glu Thr Ser Thr Glu Lys Glu Ala Asp Gly Lys Thr
                 20                  25                  30

Ser Pro Gln Cys Glu Pro Gly Cys Ile Gly Asn Tyr Gln Pro Cys Ile
                 35                  40                  45

Glu Ser Thr Lys Pro Cys Cys Arg Leu Glu Asp Arg Thr Ser Val Gln
         50                  55                  60

Phe Gly Arg Lys Glu Tyr Ile Cys Asp Arg Phe Phe Gly Gly Leu Cys
 65                  70                  75                  80

Ala Pro Leu Asp Val Ile Asn Asn Leu Thr Leu Tyr Lys Glu Leu Ser
                 85                  90                  95

Ala Gln Leu Asn Glu Thr Asn Leu Ala Glu Leu Ser Asn Leu Tyr Phe
                 100                 105                 110

Gln Gly Ile Lys His Thr Leu Gly Ile Lys Pro Glu Pro Lys Ile Glu
         115                 120                 125

Asp Ala Gly Lys Val Glu Gly Val Val Lys Gln Ser Thr Asp Asn Met
 130                 135                 140

Lys Leu Ser Thr Glu Ala Glu Arg Glu Pro Gly Asp Lys Thr Val Ser
 145                 150                 155                 160

Gly Thr Glu Asn Trp Val Gln Ser Pro Asp Thr Asp Ser Pro Ile Asn
         165                 170                 175
```

Figure 2a: SEQ ID NO:3:

Asn Lys Pro Cys Ile Glu Ser Thr Glu Ser Arg Cys Arg Leu Glu Asn
            180                 185                 190

Arg Thr Leu Val Gln Phe Gly Arg Glu Asp Ile Tyr Gly Arg Phe
        195                 200                 205

Leu Phe Phe Ile Tyr Ala Pro Leu Ile Val Val Asn Asn Ser Thr Leu
            210                 215                 220

Tyr Leu Glu Leu Ser Lys Gly Met Asn Glu Thr Lys Leu Ser Asn Leu
225                 230                 235                 240

Ser Asp Trp Tyr Ile Ala Ala Ala Val Ile Pro Met Pro Glu Phe Lys
            245                 250                 255

Pro Glu Ser Lys Ile Glu Asp Glu Arg Lys Ser Pro Glu Ala Pro Glu
        260                 265                 270

Leu Glu Ser Gln Cys Ile Pro Asn Tyr Glu Leu Cys Val Asn Ser Lys
275                 280                 285

Arg Pro Cys Cys Trp Glu Asn Lys Leu Phe Ala Gly Ser Ser Lys Pro
        290                 295                 300

Arg Asn Phe Val Cys Gly Leu His Gly Arg Ser Tyr Cys Ser Pro Phe
305                 310                 315                 320

Asp Gly

Figure 2b: SEQ ID NO:3:

```
GTCGAACTGT ATCTCTAACG ATCACAGTAG CTCAACCCAA ACTTTTCAAA ATTTTCGCAA      60

AAATCTGTTT TTTGGTGCTT ATGTGTTGCG TGTTCGTCTA TAAAAACATC AATTTGTAAA     120

CAATTG ATG TAC AAA TTT GTT TTG GTG ACG CTT CTG AGC TGT GTG CTG        168
       Met Tyr Lys Phe Val Leu Val Thr Leu Leu Ser Cys Val Leu
        1               5                  10                 335

GCC CAA GCG AAT CCG CAG GTG TCG CGC CAT GGT CCC GCT GCT GTT GTA       216
Ala Gln Ala Asn Pro Gln Val Ser Arg His Gly Pro Ala Ala Val Val
 15              20                  25                  30

TCG GAT GCG AAT CGA ACG GTT CAT CCT CCA GCT CAA AAC CAC GCC           264
Ser Asp Ala Asn Arg Thr Val His Pro Pro Ala Gln Asn His Ala
         35                  40                  45

GAG ATG GCA CGT TTC ATC GTT AAT CAA GCC GAC TGG GCA TCT CTG GCA       312
Glu Met Ala Arg Phe Ile Val Asn Gln Ala Asp Trp Ala Ser Leu Ala
             50                  55                  60

ACA ATC AGC ACT ATA GAA AAC ATC GCT TCT TAT CCA ATT GCC AGC ATA       360
Thr Ile Ser Thr Ile Glu Asn Ile Ala Ser Tyr Pro Ile Ala Ser Ile
 65                  70                  75

AAA TCA ATT AGT GAC GGA CCG GGC AAT GGT ACC GGA GAT CCT TAT           408
Lys Ser Ile Ser Asp Gly Pro Gly Asn Gly Thr Gly Asp Pro Tyr
 80                  85                  90

TTG TTT ATC TCA CCG AGG ACT TTC TCT GGT AGA GAC ATA GTT GCT GAT       456
Leu Phe Ile Ser Pro Arg Thr Phe Ser Gly Arg Asp Ile Val Ala Asp
 95                 100                 105                 110
```

Figure 3a: SEQ ID NO:4:

```
TCG CGA GCG AGT CTC GTC ATC TCC TTG GCT CAG GGT GCC TAC TGC AAG      504
Ser Arg Ala Ser Leu Val Ile Ser Leu Ala Gln Gly Ala Tyr Cys Lys
                115                 120                 125

GAA AAT AAT TAT GAT CCA ATG GAC CCG CGA TGC GGA AGA GTT GTC ATC      552
Glu Asn Asn Tyr Asp Pro Met Asp Pro Arg Cys Gly Arg Val Val Ile
            130                 135                 140

ACC GGG AGC CGA AAA AAT TGG GGA ATC CAG CCT CCG AAT ACC GCA          600
Thr Gly Ser Arg Lys Asn Trp Gly Ile Gln Pro Pro Asn Thr Ala
        145                 150                 155

AGA GCC AGG ACT GCT TTC TTC GGA CGT CAT CCC GCG ATG NCC TAT ATG      648
Arg Ala Arg Thr Ala Phe Phe Gly Arg His Pro Ala Met Xaa Tyr Met
        160                 165                 170

CCT AGA GAT CAT GGT TTC TAC TTC GCG AAA ATA AAC ATT GAA AAT CTT      696
Pro Arg Asp His Gly Phe Tyr Phe Ala Lys Ile Asn Ile Glu Asn Leu
175                 180                 185                 190

CGT GTT CTT GCA TCA TTT GGT CCA TTC CAC GTG GTC TCC GCT CAA GAT      744
Arg Val Leu Ala Ser Phe Gly Pro Phe His Val Val Ser Ala Gln Asp
            195                 200                 205

TAC TAC AGT GCA TCG GTT GGA CAG CGA CAA GAT TGN ATG TAT TCA CTA      792
Tyr Tyr Ser Ala Ser Val Gly Gln Arg Gln Asp Xaa Met Tyr Ser Leu
                210                 215                 220

TAT ACG AGT GTA CAA ATT GCA CTT CGG TAATTTGAGA AAGTTCAATC            839
Tyr Thr Ser Val Gln Ile Ala Leu Arg
            225                 230

ATATTTGACT CTCCGAGGAA CNCGATACTG TTGAAATAAA ATC                      882
```

Figure 3b: SEQ ID NO:4:

Figure 4

VIRAL AND INSECT GENES THAT INHIBIT THE IMMUNE SYSTEM AND METHODS OF USE THEREOF

GOVERNMENT LICENSE RIGHTS

The U.S. Government has a paid-up license in this invention and the right in limited circumstances to require the patent owner to license others on reasonable terms as provided for by the terms of Grant No. AI-33114-03 awarded by the National Institutes of Health, Department of Human Services.

FIELD OF THE INVENTION

The invention relates to the new genes, particularly viral, endoparasitic insect and insect host genes, encoding products that specifically inhibit the insect immune response. The invention further relates to methods of expanding the host range of insect viruses and methods of biological control of plant insect pests using the genes of the invention. The invention is thus useful, for example, in the biological control of insect pests and, in particular, in the protection of crops from insect damage.

BACKGROUND OF THE INVENTION

Insects, like other animals, have effective immune systems to combat both biotic and abiotic foreign invasion. It is of interest, then, that certain insect species, the endoparasitic insects, spend a part of their life cycle inside the body of other insect hosts. Considerable effort has been expended investigating the mechanism by which these endoparasitic insects avoid the host immune system in this parasitic relationship.

Mechanisms of "immune evasion" include (1) avoidance (e.g., by not coming into prolonged contact with the immune system), (2) evading the immune system, for example, by molecular mimicry, (3) blocking the immune recognition system, (4) subversion of the host immune system, and (5) suppression of the immune system. (Vinson, UCLA Symposia on Molecular and Cellular Biology, 112: 517 (1990)). For large foreign bodies, in particular, encapsulation by the granulocytes and plasmatocytes of the hemolymph is a common immune response.

It is currently thought that encapsulation results from a first recognition of the foreign body surface by the granulocytes, which then degranulate to release one or more chemoattractant substances that are assumed to attract additional granulocytes and plasmatocytes. The plasmatocytes then attach to the foreign body, flatten out and form a microtubule and microfilament matrix, ultimately enclosing the foreign body in several layers of cells. In some cases, the inner layers of plasmatocytes melanize. Encapsulation thus serves to isolate the foreign body in the insect.

One well characterized parasitoid-host system in which there is immune system evasion is that of the endoparasitic wasp *Campoletis sonorensis* and its host, the tobacco budworm *Heliothis virescens*. In investigating how immunosuppression is regulated in this system, it became apparent that a group of wasp viruses, known generically as polydnaviruses, play a role in the suppression of the host immune system. It is believed that during oviposition, the endoparasitic insect, for example *C. sonorensis,* injects not only eggs but also polydnavirus and oviduct proteins. Shortly thereafter, the host insect immune system begins to show evidence of altered activity and the endoparasitoid eggs remain free from encapsulation. The precise mechanism of this immune suppression is not, however, presently known but may involve disruption of the hemocyte cytoskeleton.

Additional factors in immune system suppression may be contained in the wasp oviduct fluid and venom. It is also known that insect venom, ovarian and viral proteins share certain epitopes and that one or more ovarian proteins transiently inhibits the immune response (Webb and Luckhart, Archives of Insect Biochemistry and Physiology, 26: 147 (1994)).

It has been shown that oviduct proteins may, at least in part, mediate the immunosuppressive effect observed in some systems. Additionally, the effect can be generated by the injection of purified polydnavirus particles and virus-like particles (VLPs). For example, VLPs (which are devoid of nucleic acids) are thought to be involved in the suppression of the immune response in *Venturia cansecens.* (Schmidt et al., Subcell. Biochem., 15: 91 (1989)). Certain VLP proteins may be related to a host protein, designated p42, in this system. Another report indicates interference of plasmatocyte-dependent immune phenomena by polydnavirus-rich calyx fluid. (Davies et al., Cell and Tissue Research, 251: 467 (1988)) It is conjectured that successful parasitism may require immunosuppression of the host to a level that interferes with other cellular immune reactions in addition to encapsulation.

Host cellular factors may also be involved in the immune suppression in some cases. For example, a cellular immunosuppressive protein factor, ISP, has been isolated from the larval plasma of the armyworm *Pseudaletia separata* parasitized with the wasp *Cotesia kariyai.* The factor, which suppresses encapsulation of foreign bodies, is suggested to be a 470 kDa hexamer composed of identical 82 kDa subunits. (Hayakawa, J. Biol. Chem., 269:14536 (1994)).

Thus, depending upon the particular system studied, host, parasite and/or virus factors may be involved in the suppression of the host immune system. (Vinson, Archives of Insect Biochemistry and Physiology, 13: 1 (1990)). It is therefore believed that each of these sources may play a role in host insect immune system suppression generally, and that there may be a cooperative effect between factors which allow the immune system to be compromised sufficiently for parasitization.

The WHv1.0, WHv1.6 and VHv1.1 genes of *Campoletis sonorensis* polydnavirus (CsPDV) have recently been cloned and sequenced. These genes are described as members of a polydnavirus "cysteine-rich" gene family. (Dib-Hajj et al., Proc. Natl. Acad. Sci. (USA) 90: 3765 (1993)). It has been conjectured that these genes may play a role in preventing the recognition of foreign objects and/or the normal response of components of the immune system. (Summers et al., Proc. Natl. Acad. Sci. (USA) 92: 29 (1995)). Indeed, the VHv1.1 gene product of the *C. sonorensis* polydnavirus has been implicated in the inhibition of the cellular immune response. This 30 kDa protein is shown by indirect immunofluorescence to bind both granulocytes and plasmatocytes and is thought to inhibit encapsulation. (Li et al., J. Virol., 68: 7482 (1994)).

As parasitoid insects eventually kill their insect hosts, the parasitoids represent a natural biological means for controlling insect pests, in particular those pests responsible for crop damage. Traditionally, such parasitoids have not provided a highly effective strategy for insect control, in large part because the host range of the parasitoids is limited.

It would therefore be advantageous to provide methods whereby the host range of parasitoid insects could be broadened, such that the parasitoids would provide effective biological control for a larger number of insect hosts.

It would be a further advantage to identify specific virus, parasitoid and/or host genes involved in the successful suppression of the insect immune system by the endoparasitoid. Such genes could then be used, through recombinant DNA techniques, to generate genetically modified insects, viruses and/or plants, that express one or more immune suppressing factors.

The invention provides these and other advantages, as will be apparent to those skilled in the art based on the disclosure hereunder.

SUMMARY OF THE INVENTION

The invention first provides a DNA useful for the suppression of an insect host immune system. In particular, the invention provides the VHv1.4 genomic DNA, derived from the C. sonorensis polydnavirus, and the sequence of which is set forth in SEQ ID NO: 1. The invention further provides a VHv1.4 cDNA (SEQ ID NO: 2), which encodes the VHv1.4 protein product (SEQ ID NO: 3) involved in insect immune system suppression. The invention also provides the SOPs cDNA (SEQ ID NO: 4) of Campoletis sonorensis and the protein encoded thereby (SEQ ID NO: 5), also useful in suppressing the insect immune system in the methods of the invention. Each of these DNAs and protein is useful for the expansion of viral host range.

The invention further provides methods for expanding parasitoid insect host range comprising:

providing one or more DNAs encoding an insect immune suppressing factor, or a biologically active fragment thereof, operably linked to one or more expression signals, inserting said DNA into the genome of an endoparasitic insect virus, an endoparasitoid or a plant, and expressing said DNA to provide for immune suppression of one or more insect hosts, wherein the insect hosts are not a natural host for said endoparasitic insect.

The invention additionally provides for genetically modified viruses, particularly polydnaviruses, endoparasitoid insects and/or plants capable of expressing a DNA encoding an immunosuppressive protein or polypeptide.

The invention also provides plasmids, vectors and, especially, expression vectors operably linked to the DNA of the invention.

The invention yet further provides a recombinant protein encoded by a DNA, or biologically active fragments thereof, wherein said protein or fragment suppresses the immune system of one or more insect hosts, as well as methods of broadening the host range of insect viruses and parasitoids comprising applying the protein or fragment to plants, whereby said protein is ingested by said pests.

The invention further provides methods of protecting crops, particularly commercially important crops, from damage by one or more insect pests.

DETAILED DESCRIPTION OF THE INVENTION

Genes that disrupt the insect immune system are of practical importance in the area of biological pest control. Specifically, the insect immune system is thought to determine the host range of the group of insect viruses known as baculoviruses. Additionally, virus host range is a major factor in determining whether a particular virus will be of commercial importance. Genes that suppress the immune system and thereby expand the virus host range would significantly improve the commercial prospects and performance of insect viruses as a biological pest control means. Immune suppressive genes under the invention provide for methods in which viruses, for example baculoviruses, can be used for expression, with the concomitant immune suppression and expansion of the virus host range.

The endoparasitic wasp Campoletis sonorensis injects a polydnavirus into its host Heliothis virescens during oviposition. Viral gene expression protects the wasp egg and larva from encapsulation by host hemocytes. The invention relates to the isolation and purification of genes involved in escaping the host immune response. As exemplary of the invention, the VHv1.4 genomic and cDNA have been isolated from C. sonorensis polydnavirus. As shown below, the VHv1.4 protein is involved in suppressing the immune system of the insect host. This protein is further capable, by means of its immune system targeting function, to broaden the host range of the endoparasite and thereby provide an efficient means of pest control.

The current data indicates that the binding of immune-suppressing proteins to granulocytes and plasmatocyte surfaces is involved in immune suppression and disruption of the hemocyte cytoskeleton. The binding of hemocytes has been shown to occur in permissive and semi-permissive hosts. Moreover, the binding additionally occurs in some, but not all, non-permissive hosts. These results suggest that the host range of endoparasitic insects is related to the effectiveness by which these insects suppress the immune system of the potential host.

EXPERIMENTAL

A. Isolation of the VHv1.4 cDNA

Insect rearing and viral DNA purification from calyx fluid were done as described (Krell et al., J. Virol. 43: 859 (1982)). For RNA analysis requiring parasitized H. virescens, 15 to 20 third-instar larvae were parasitized by 8 to 10 female wasps within about 30 minutes. At the end of this period, larvae were designated as 0 hr p.p (post parasitization).

A lambda gt11 cDNA library was constructed from mRNA of parasitized H. virescens and screened by colony hybridization using the VHv1.1 cDNA as a probe (Sambrook et al. 1989). Positive hybridization plaque DNA was amplified by polymerase chain reaction (PCR) using lambda gt11 forward (5'-GGTGGCGACGACTCCTGGAGC-3') (SEQ ID NO: 6) and reverse (5'-GACACCAACTGGTAATG-3')) (SEQ ID NO: 7) primers (Tung et al. 1989). Amplification reactions were carried out in 1× PCR buffer (10 mM Tris-HCl, pH 9.0, 50 mM KCl), with 50 µM each dNTPs, 1.25 mM $MgCl_2$, 0.5 µg of each of the primers, 5 µL phage suspension and 2.5 units of Taq DNA polymerase. Phage DNA was denatured at 94° C. for 2 min. and 35 amplification cycles were performed (94° C., 2 min., 55° C., 2 min., 72° C., 3 min.) in a Model 480 DNA thermocycler (Perkin Elmer Cetus). The amplified DNA fragments were digested with EcoRI and cloned in "BLUESCRIPT" II KS(−) (Stratagene) for sequence analysis.

To clone the 3' end of VHv1.4 cDNA, 0.5 μg of total RNA from parasitized *H. virescens* larvae at 24 hr. p.p. was reverse transcribed using oligo(dT) primer (GCACTTAACT$_{17}$) (SEQ ID NO: 8). Reverse transcription was performed at 42° C. for 30 min. in 20 μL of reaction mix containing 1× cDNA synthesis buffer (50 mM Tris-HCl, pH 8.9, 20 mM KCl, 2.5 mM MgCl$_2$, 200 μM of each dNTP, 10 mM DTT, 0.2 μg primer and 200 units MMLV reverse transcriptase (Promega)). The reaction mixture was digested with 2 units of RNAse H at 42° C. for 10 min. One microliter of the reverse transcription mixture was removed for PCR with oligo(dT) and 1.4 kb cDNA-specific primers, using 35 cycles of 94° C., 1 min., 48° C., 1 min., 72° C., 2 min. The PCR product was cloned in the pCR-TRAP vector (GeneHunter) for sequence analysis.

B. Isolation of the VHv1.4 Genomic DNA

The viral genomic copy of the VHv1.4 gene was cloned from a 12.9 kb EcoRI fragment of SH V, contained in pVE12.9 cloned in pBS (Dib-Hajj et al. 1993). This clone was used to screen a CsPDV PstI library in "BLUESCRIPT" KS(−) to select an overlapping 7.9 kb clone (pVP7.9) that hybridized to both termini of pVE12.9. Another CsPDV Sau3A library made from partially digested viral DNA was probed with the 0.8 kb fragment of the 1.4 kb cDNA. Clones hybridizing to the probe were re-screened by PCR with 1.4 kb-specific primers. Amplification was performed with the GeneAmp 6000 system (Perkin Elmer Cetus) using the following protocol: 94° C., 2 min., 94° C., 30 sec., 55° C., 30 sec., 72° C., 1 min., for 35 cycles. Overlapping SH V genomic clones were mapped with restriction enzymes.

E. DNA Sequencing and Analysis

DNA sequences were determined by the dideoxy chain termination method (Sanger et al. 1977) using "SEQUE-NASE" 2.0 kit (United States Biochemical) . Sequence data were analyzed using the University of Wisconsin Genetics Computer Group DNA analysis software for the VAX computer (release 7.2).

Figure 2A:
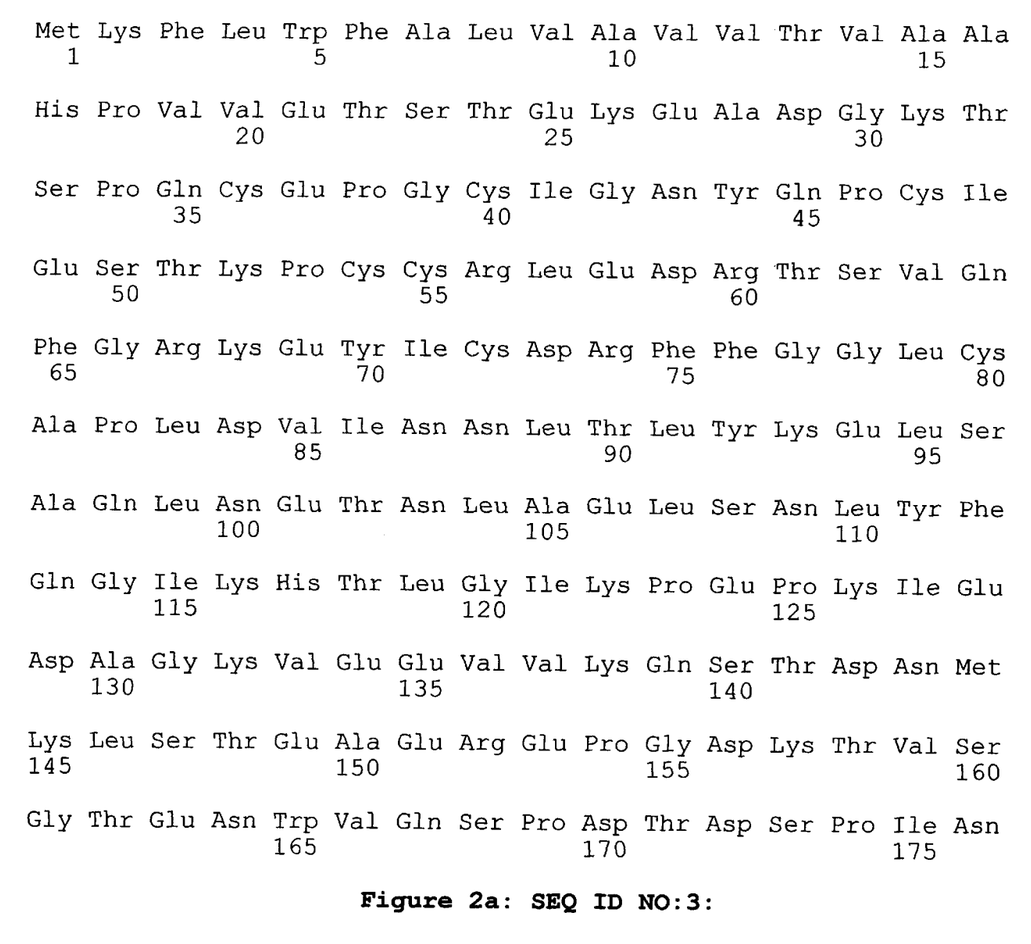
FIG. 2 depicts the predicted amino acid sequence (SEQ ID NO: 3) encoded by the VHv1.4 cDNA sequence (SEQ ID NO: 2).
Figure 2B:
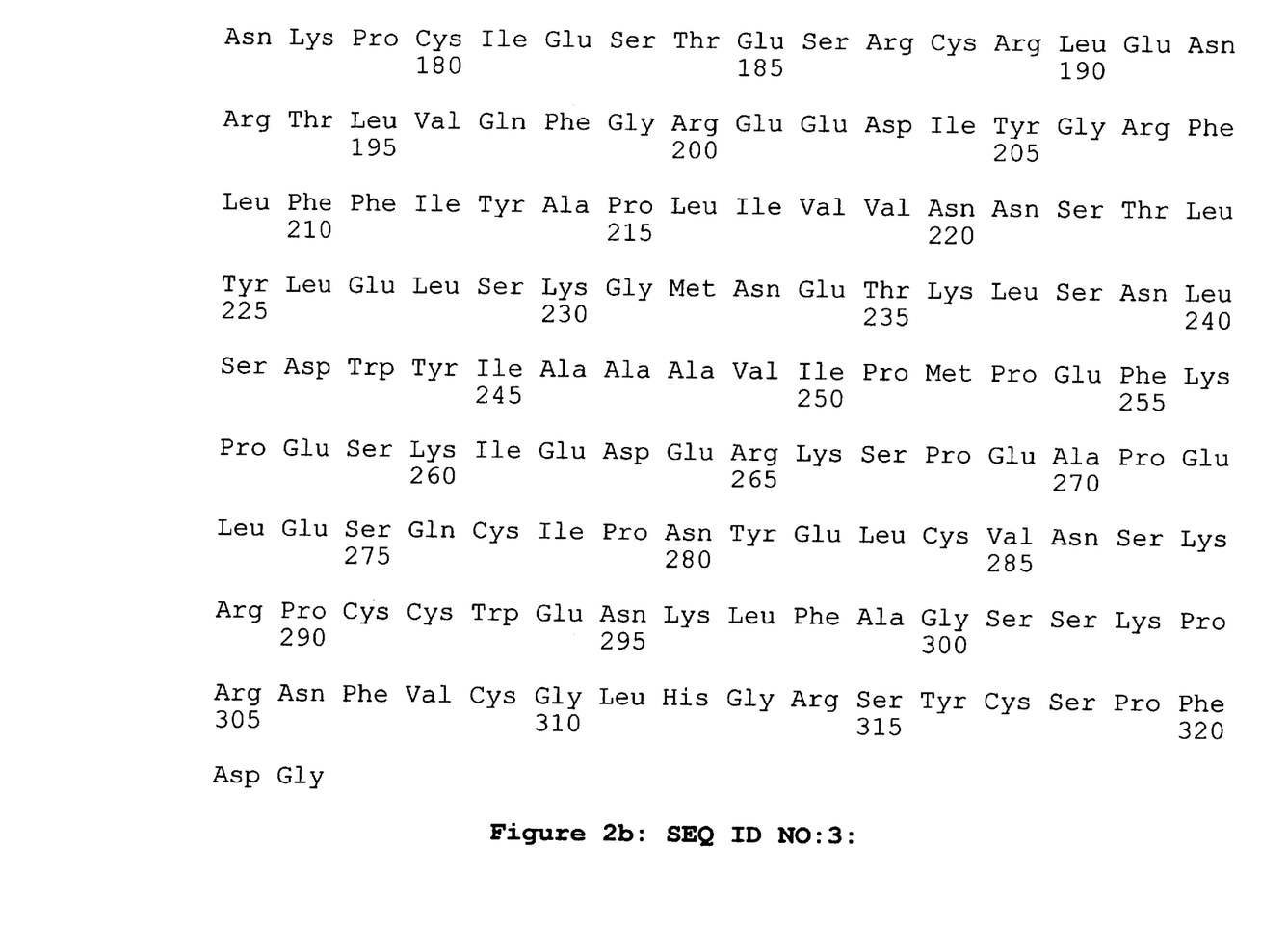
Figure 3A:
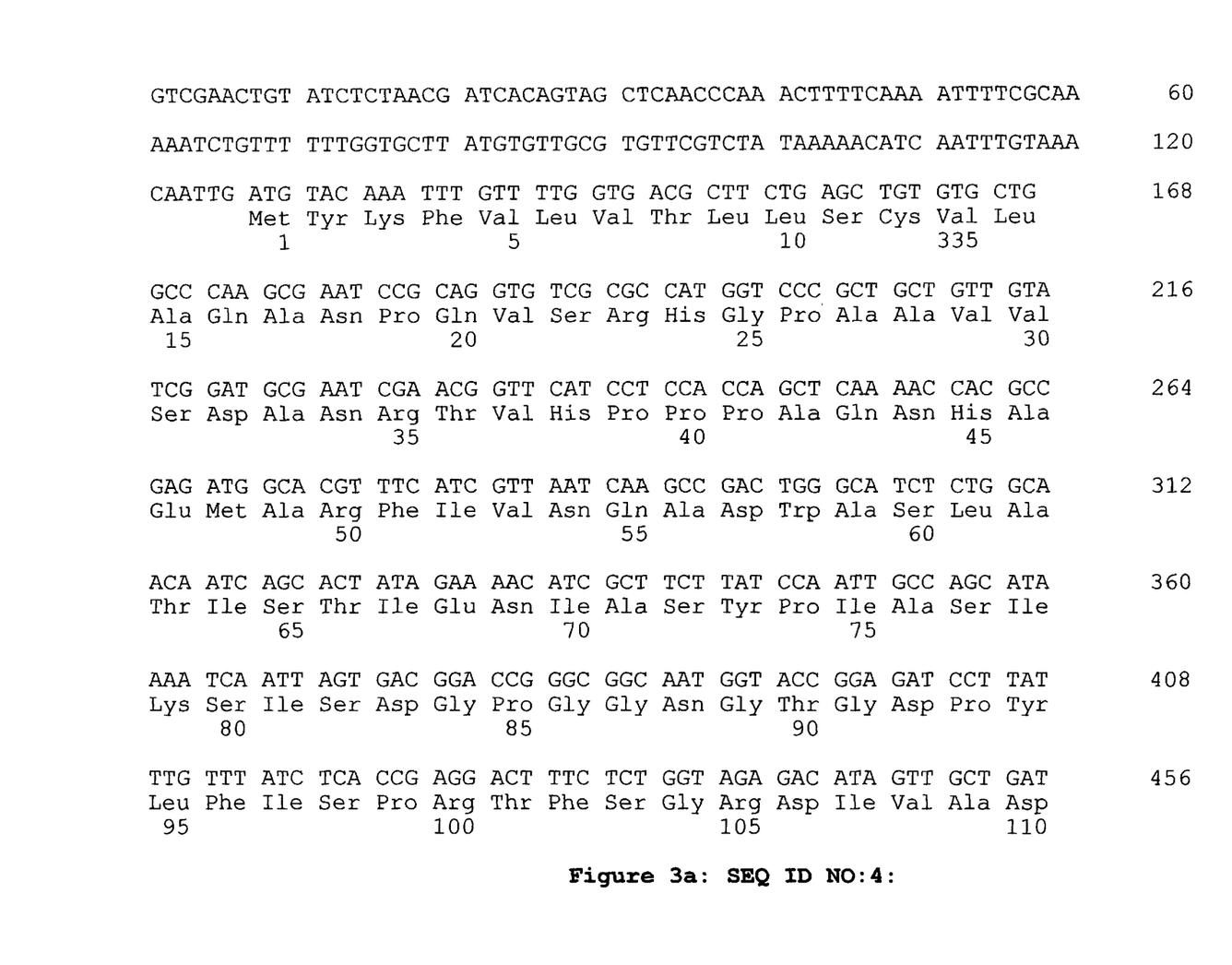
FIG. 3 depicts the C. sonorensis SOPs cDNA SEQ ID NO: 4 and the protein product (SEQ ID NO: 5) encoded thereby.
Figure 3B:
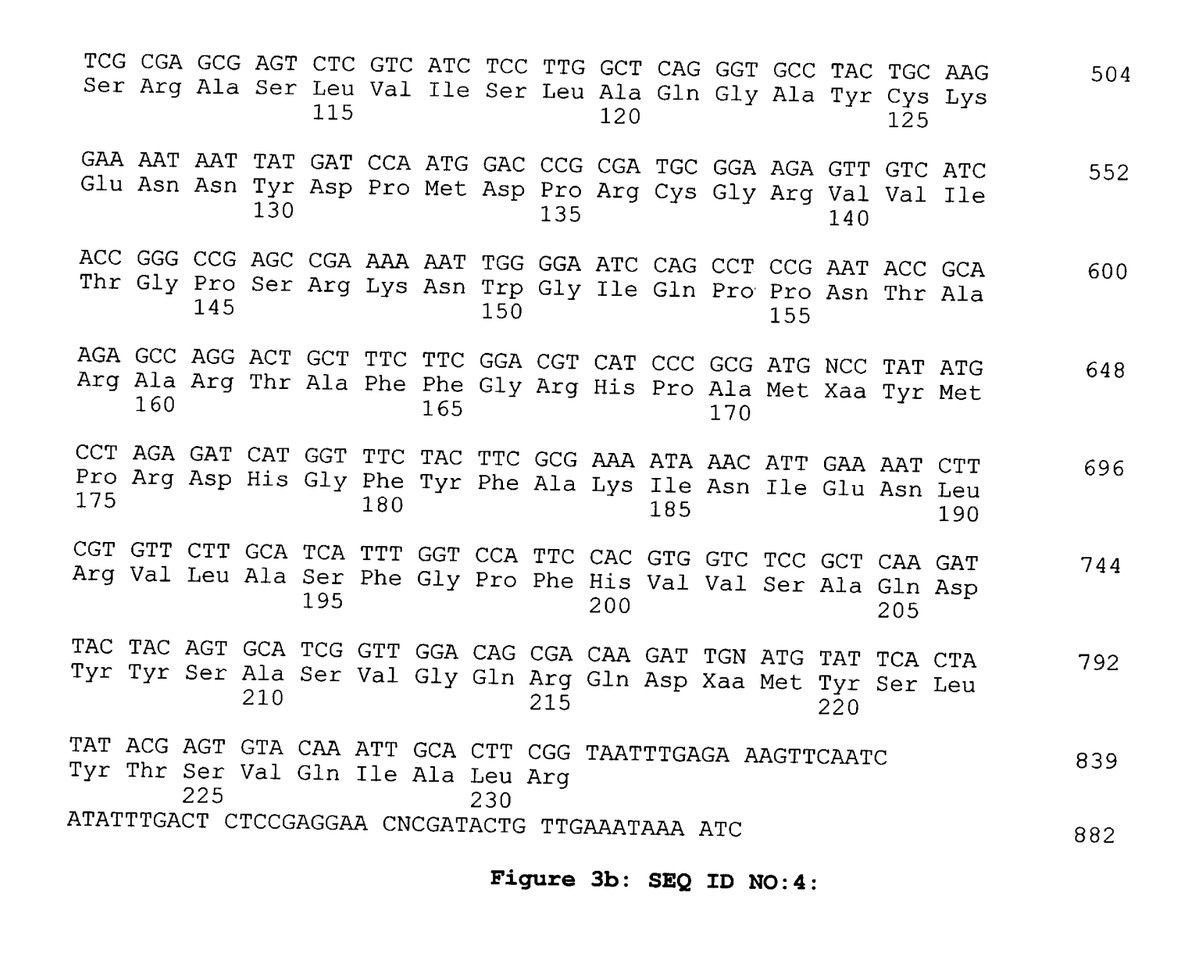
Figure 4:
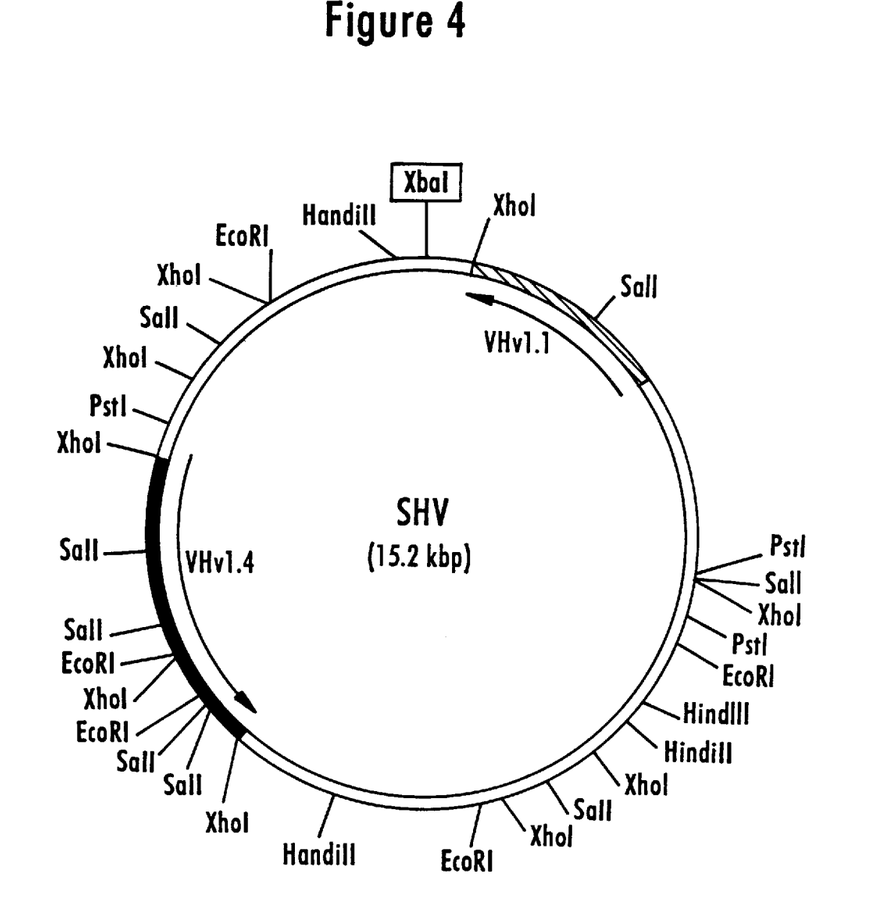
FIG. 4 schematically depicts the plasmid pSH V.

The predicted amino acid sequence of the longest ORF of the VHv1.4 cDNA insert is given (SEQ ID NO: 3). The cDNA sequence is 1338 bp long, and the longest ORF identified is 966 nt from nucleotide 57 (relative to the 5' end of the cDNA clone) to nucleotide 1022. The sequence surrounding the first methionine codon in the cDNA is consistent with the translation initiation consensus sequence (Kozak 1983). A putative polyadenylation signal is located 15 nt upstream from the poly(A) tail.

The longest ORF in the 1.4 kb cDNA encodes a protein of 322 amino acids with a predicted molecular mass of 42 kDa. The N-terminal amino acid sequence is very hydrophobic and encodes a signal peptide according to the rules of von Heijne, indicating that this protein is destined either for insertion into the membrane or secretion. There are six potential N-glycosylation sites in the protein and, similar to the VHv1.1 cDNA, there are two complete cysteine motifs (amino acids 40 to 80 and 277 to 317).

Figure 1A:
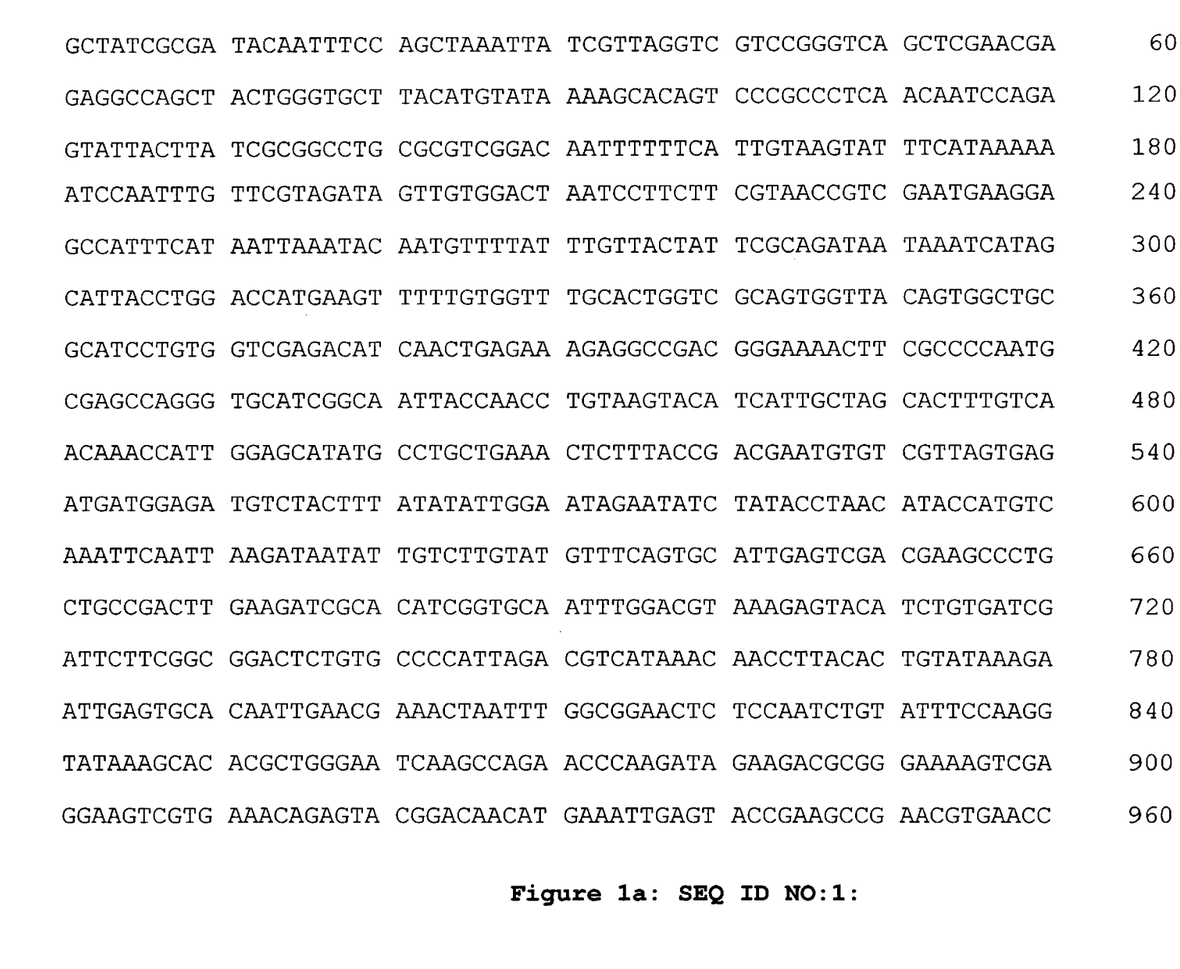
FIG. 1 depicts the genomic DNA sequence of the C. sonorensis polydnavirus VHv1.4 DNA (SEQ ID NO: 1).
Figure 1B:
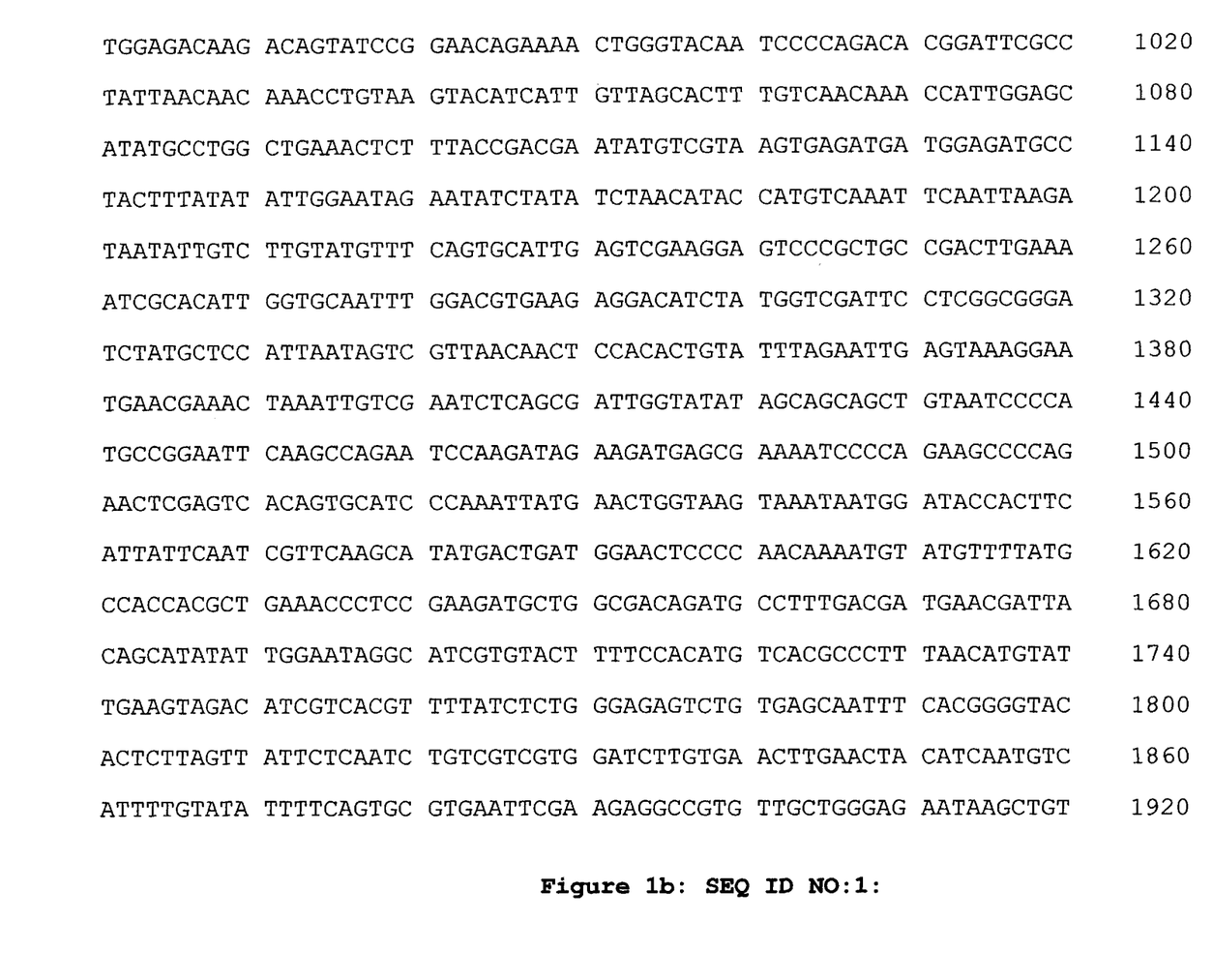
Figure 1C:
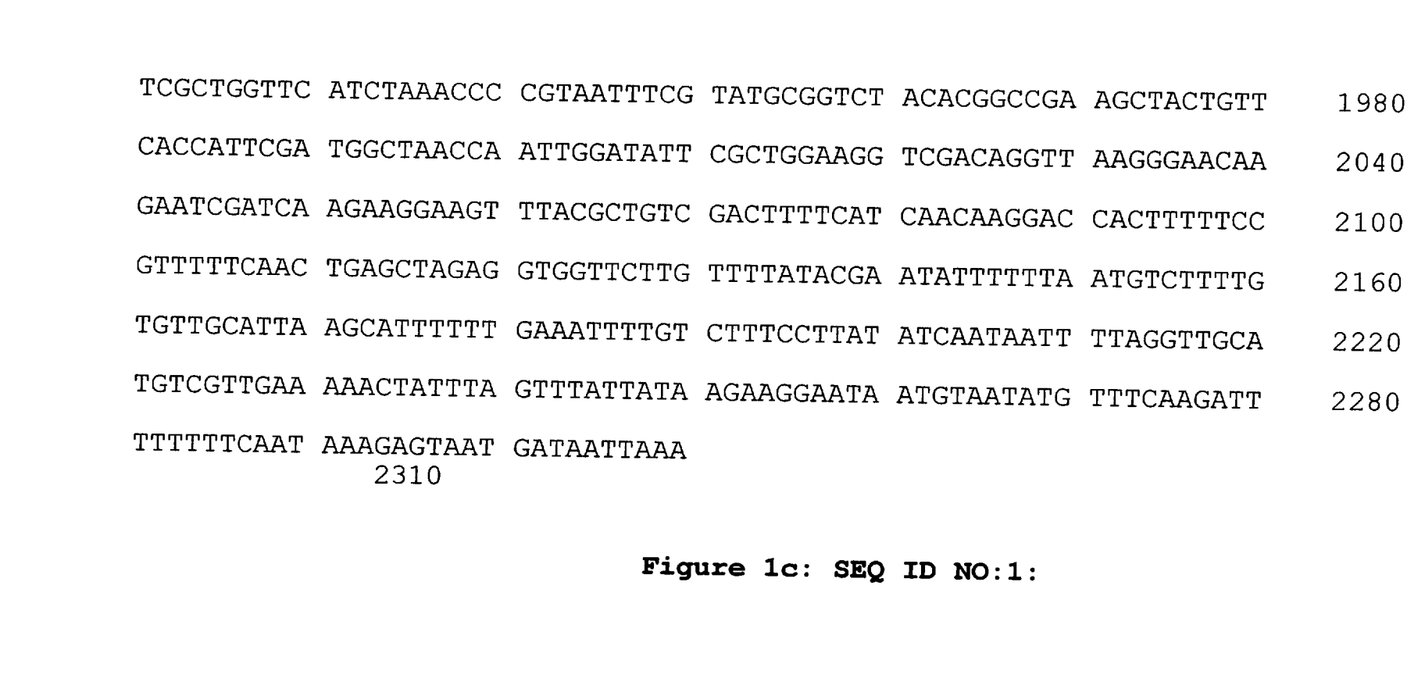

The genomic clone was determined by Southern hybridization to reside on a 2.7 kb XhoI genomic fragment. This 2.7 kb fragment was sequenced, confirming that the cDNA is encoded by this genomic DNA fragment. A putative TATA box is located in the genomic DNA 42 bp upstream of the 5' end of the cDNA clone. Four introns 124, 186, 187 and 342 bp in length were identified in the genomic DNA. Splicing signals are consistent with the consensus for eukaryotic genes. Intron 1 is found in the 5' leader region, 27 bp upstream of the translation initiation ATG. The three other introns lie within the coding sequence.

F. Inhibition of the Immune Response by the VHv1.4 Gene Product

To demonstrate that the VHv1.4 gene product inhibits host immune response, the cDNA and genomic clone are inserted into bacterial expression vectors operably linked to transcription control signals. A suitable vector for such expression is pET22b(+), which allows the fusion with a 6× histidine tag to facilitate purification. Such construction is suitably made by attachment of, for example, EcoRI linkers to the VHv1.4 DNA and insertion into EcoRI site of the vector by standard procedures. The expressed product from the vector is thus a fusion that facilitates purification.

After transformation of a suitable bacterial host, (e.g. *E. coli*), expression of the fusion protein is induced with IPTG and purified from the bacterial lysates. The fusion protein can be engineered, where desired, to contain a unique protease cleavage site at the fusion junction. For example, a Factor Xa cleavage site may be used, allowing isolation of intact or nearly intact VHv1.4 protein. As is known to the skilled artisan, this purified protein can also be used for immunization to raise antibodies against one or more antigenic determinants.

The VHv1.4 cDNA or genomic DNA may also suitably be expressed in a baculovirus system. The recombinant DNA is cloned into a suitable vector, for example pVL1393, and cotransfected with the E2 strain of *Autographa californica* nuclear polyhedrosis virus into *Spodoptera frugiperda* (Sf9) cells to produce a recombinant virus. This virus may then be assayed according to standard procedures (Webb et al. 1990).

To demonstrate the immunosuppressive function of the VHv1.4 protein, washed eggs are prepared from 20 chilled *C. sonorensis* female wasps. The eggs are suitably dissected from wasp ovaries about 5 days after mating. Eggs are suspended in 1 mL of Pringle's saline and collected by centrifugation (1500×g, 7 min.). Eggs are then resuspended in Pringle's saline and pelleted about five times to remove CsPDV and ovarian proteins. Recombinant virus (10$^4$ PFU) in a volume of about 1 μL is injected into chilled fourth-instar *H. virescens* larvae with a 10 μL Hamilton microsyringe. The E2 stain of wild-type virus or a saline solution can be injected into additional larva as controls to which the activity of the recombinant virus can be compared. Naturally parasitized insects may also be used as a control.

Twenty four hours post injection, pretreated larvae are injected with washed wasp eggs (8 to 12 eggs/larva) with a finely drawn glass capillary. The encapsulation response to the eggs is then determined. In the absence of virus and ovarian proteins, a strong encapsulation response to parasite eggs is seen at about 24 hours post injection. If, at 24 hours post parasitization, one or more of the eggs had 100 or more adherent hemocytes, covering at least one third of the egg, then the host is scored as immunoresponsive. If fewer than 100 hemocytes are adhered on all the eggs recovered, then the insect is scored as immunosuppressed. These data can then be analyzed by chi-square statistical analysis.

The above-described experiment demonstrates that the VHv1.4 protein inhibits the host immune response. Thus, vectors expressing the VHv1.4 protein, or biologically active fragments thereof, and other toxic proteins may be useful in biological pest control. For example, inclusion in the vector of an expression cassette for scorpion toxin and/or other toxins, coupled with the immune suppression of the pest, allows for a faster and more efficient kill of the pests.

It is thus another embodiment of the invention to have a vector, preferably a baculovirus vector, containing a DNA which encodes an immune-suppressing protein or fragment thereof, preferably the VHv1.4 cDNA, genomic DNA, or a biologically active fragment thereof, and one or more genes encoding a polypeptide or protein possessing a toxic activity. A suitable vector for use in this embodiment of the invention is the above-mentioned pVL1393 baculovirus vector. Expression of the immune-suppressing sequences in a recombinant virus, a parasitoid, a host or a plant is used to affect biological control of the insect pest.

In yet another embodiment of the invention, the VHv1.4 cDNA, genomic DNA or biologically active fragment thereof, is introduced into plants to create transgenic plant varieties. Such plants, when producing the VHv1.4 protein or biologically active fragment thereof, become resistant to insect pests. According to this embodiment of the invention, a transgenic plant capable of expressing an immune suppressing protein or polypeptide, is made by any of the known techniques using the DNA of the invention. Insect larva feeding on such transgenic plants become immune suppressed and thus susceptible to a large variety of diseases.

A further embodiment of the invention is directed to use of the VHv1.4 protein, or a biologically active fragment thereof, for direct application onto plants. In this embodiment, the VHv1.4 protein is overexpressed, for example, in bacteria, yeast, plants, insect cells, etc., isolated and purified. In one preferred embodiment, the protein or fragment thereof is produced as a fusion with an amino acid sequence that assists in purification. Preferably, a poly-histidine linker is used for a N- or C-terminal fusion product, thereby allowing rapid isolation and purification of the fusion protein. Most preferably, the poly-histidine linker comprises about 7 contiguous histidine residues and may be removed by endoproteolytic enzymatic cleavage.

The recombinant protein so produced may be conveniently lyophilized to increase storage life or, as one alternative, may be kept in a buffered solution, for example, phosphate buffered saline. The product so produced is then applied to plants, preferably after reconstitution of the lyophilized product in water or buffered saline. In practice, insect larva ingest the recombinant protein and become immune suppressed, thereafter being susceptible to lethal infections.

As examples of other genes useful in the practice of the invention, mention is made to the *C. sonorensis* OPs 33 genes, in particular the SoPs gene (SEQ ID NO: 4), and the *C. sonorensis* polydnavirus WHv1.0, WHv1.6, VHv1.1 and 2.6 kb RNA genes, as well as functionally related genes from virus, endoparasitoids and hosts. Following the disclosure herein, other genes related to the above-mentioned genes can be isolated by, for example, library hybridization, PCR and reverse transcription technologies. Such genes are therefore meant to be embraced within the scope of the present invention.

The invention further is useful for increasing the host range of endoparasitic pests. In this embodiment, a recombinantly engineered virus, preferably a baculovirus, is constructed to express an immune suppressing protein, preferably VHv1.4 protein, or a biologically active fragment thereof. A variety of endoparasitic pests are then produced which are capable of expressing the recombinant virus. Upon oviposition, the immune suppressing protein (e.g., VHv1.4 protein) is expressed, leading to the suppressing of the host immune system. As above, such a recombinant virus may also encode one or more toxic substances, to increase the speed and efficacy of the insect kill.

In these and other embodiments of the invention, the parasitoid host range is broadened to include non-natural host insects. By "non-natural" it is meant that the host insect is not the naturally-occurring host for the particular endoparasitoid insect.

Additionally, vectors under the invention may also encode a marker for the rapid identification of recombinant virus, endoparasite, host or plant. Such a marker may provide a visible result (e.g., β-galactosidase, luciferase, etc.) or may be either a positive or a negative selectable marker.

The invention is exemplified by the VHv1.4 gene of the *C. sonorensis/H. virescens* parasitic system. It is by no means meant, however, to be restricted to this system. For example, there are tens of thousands or insect species, many if not all of which are expected to contain viruses that function analogously to the *C. sonorensis* polydnavirus in suppressing the host immune response. Moreover, certain toxins and oviduct proteins are also believed to have immune suppressing function. Each of these immune suppressing proteins, which may be related by a common cysteine motif (Dib-Hajj et al., Proc. Natl. Acad. Sci. (USA) 90: 3765 (1993)), are within the scope of the invention.

Representative insect species that may be biologically controlled by the process of the invention include:

*Autographica californica, Heliothis virescens, Heloithis zea, Spodoptera frugiperda, Peridroma saucia, Prodenia eridonia, Prodenia ornithogalli, Pseudaletia unipuncia, Spodoptera exigua, Trichoplusia ni, Agrotis ipsilon, Estigmene acrea, malacosoma pluviale, Nomophila noctuella, Pieris rapae, Prodenia praefica, Ceramica picta, Dargida procincta, Feltia sp., Grapholithya molesta, Heliothis armigera, Heliothis assulta, Hymenia recurvalis, Lacinipolia stricta, Miselia sp, Morrisonia confusa, Neleucania sp., Neuris sp., Plusia sp., Ostrinia nubilalis, Vanessa atalanta* and the like.

Similarly, representative endoparasitoids which may be genetically modified or which may carry genetically modified virus under the invention include those of the order Hymenoptera, particularly of the families Braconidae and Ichneumonidae.

As will be appreciated by those skilled in the art, the invention provides for protection of one or more crops. Most notable as the commercially important crops protected are corn (maize), sorghum, beet, cotton, tomato, tobacco, sunflower, soybean, rapeseed, groundnuts, chick pea, safflower, beets, cabbage, broccoli and cauliflower and the like.

As previously noted, the invention as presently disclosed is exemplified by the *C. sonorensis* polydnavirus VHv1.4 gene and protein product, as well as biologically active fragments thereof. Such a biologically active fragment preferably contains at least one of the above-mentioned cysteine motifs. Another biologically active fragment, for example, is the protein product produced devoid of the hydrophobic N-terminal sequences and DNA encoding such a protein. Additionally, a homolog of the DNAs and proteins of the invention are within the scope of the claims appended hereto. Such a DNA homolog, for example, is one that makes use of the degeneracy of the genetic code to provide a DNA of differing sequence from that disclosed herein by that at the same time encodes the same, or substantially the same, protein product.

As discussed above, the VHv1.4 gene encodes two cysteine motifs. Based upon these motifs, one of ordinary skill in the art can design probes to search for other members of this gene family in other viruses, insect hosts and other species (e.g. arachnids). Such genes can be screened for immune suppressing activity, for example as detailed above, and used in the methods under the invention in a fashion analogous to the use of the VHv1.4 gene exemplified herein. Such immune suppressing genes may also be used in combination under the practice of the invention, to create numerous immune suppressing products for the control of insect pests.

It is a further aspect of the invention, then, to use the immune suppressing VHv1.4 gene in combination with other genes that affect an immune-suppressing response. When used in such a combination, the host range for a given parasitoid may be even more greatly expanded. Examples of such other genes are given above and include those analogous immune-suppressing genes from other parasitoid/host systems and other species under the invention. Such combinations of genes may be encoded, for example, in a single vector, on separate vectors, or incorporated into the virus, parasitoid and/or plant genome.

The above examples are meant to be exemplary of the invention, and should not be construed as a limitation to the claims appended hereto. Moreover, the scope and spirit of the invention as defined in the claims is meant to encompass those variants thereof which are obvious to those of ordinary skill in the art in light of the disclosure contained herein.

Publications and patents cited above are each incorporated herein in their entirety by reference thereto.

We claim:

1. A recombinant DNA comprising SEQ ID NO: 1 or a biologically active fragment or homolog thereof, wherein the encoded product suppresses the immune system of one or more insect species.

2. The recombinant DNA according to claim 1, wherein said DNA is isolated from the *C. sonorensis* polydnavirus.

3. A method of inhibiting the immune response of a host insect comprising:

providing a bacterial expression vector or recombinant baculovirus containing the DNA according to claim 1 operably linked to one or more expression signals; and introducing the bacterial expression vector or recombinant baculovirus and one or more endoparasitoid insect eggs into said host insect, whereby said DNA is expressed thereby inhibiting the immune response of said host insect.

4. A vector comprising the recombinant DNA according to claim 1.

5. A recombinant DNA encoding SEQ ID NO: 3 or a biologically active fragment thereof, wherein the encoded product suppresses the immune system of one or more insect species.

6. The recombinant DNA according to claim 5, wherein said DNA is isolated from the *C. sonorensis* polydnavirus.

7. A method of inhibiting the immune response of a host insect comprising:

providing a bacterial expression vector or recombinant baculovirus containing the DNA according to claim 5 operably linked to one or more expression signals; and introducing the bacterial expression vector or recombinant virus baculovirus and one or more endoparasitoid insect eggs into said host insect, whereby said DNA is expressed thereby inhibiting the immune response of said host insect.

8. A vector comprising the recombinant DNA according to claim 5.

9. The vector according to claim 8, further comprising at least one DNA sequence encoding a toxin.

10. The method of claim 7, wherein said DNA is isolated from the *C. sonorensis* polydnavirus.

11. The method of claim 7, wherein said insect eggs are from *C. sonorensis*.

12. The method of claim 3, wherein said DNA is isolated from the *C. sonorensis* polydnavirus.

13. The method of claim 3, wherein said insect eggs are from *C. sonorensis*.

14. The vector according to claim 4, further comprising at least one DNA sequence encoding a toxin.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 2310 base pairs
        ( B ) TYPE: nucleic acid
        ( C ) STRANDEDNESS: double
        ( D ) TOPOLOGY: unknown     ( i i ) MOLECULE TYPE: DNA (genomic)

( i i i ) HYPOTHETICAL: NO

( i v ) ANTI-SENSE: NO

( v i ) ORIGINAL SOURCE:
        ( A ) ORGANISM: Campoletis sonorensis virus     ( v i i ) IMMEDIATE SOURCE:
        ( B ) CLONE: VHv1.4

( x i ) SEQUENCE DESCRIPTION: SEQ ID NO:1:

```
GCTATCGCGA  TACAATTTCC  AGCTAAATTA  TCGTTAGGTC  GTCCGGGTCA  GCTCGAACGA      60
GAGGCCAGCT  ACTGGGTGCT  TACATGTATA  AAAGCACAGT  CCCGCCCTCA  ACAATCCAGA     120
GTATTACTTA  TCGCGGCCTG  CGCGTCGGAC  AATTTTTTCA  TTGTAAGTAT  TTCATAAAAA     180
ATCCAATTTG  TTCGTAGATA  GTTGTGGACT  AATCCTTCTT  CGTAACCGTC  GAATGAAGGA     240
GCCATTTCAT  AATTAAATAC  AATGTTTTAT  TTGTTACTAT  TCGCAGATAA  TAAATCATAG     300
CATTACCTGG  ACCATGAAGT  TTTTGTGGTT  TGCACTGGTC  GCAGTGGTTA  CAGTGGCTGC     360
GCATCCTGTG  GTCGAGACAT  CAACTGAGAA  AGAGGCCGAC  GGGAAAACTT  CGCCCCAATG     420
CGAGCCAGGG  TGCATCGGCA  ATTACCAACC  TGTAAGTACA  TCATTGCTAG  CACTTTGTCA     480
ACAAACCATT  GGAGCATATG  CCTGCTGAAA  CTCTTTACCG  ACGAATGTGT  CGTTAGTGAG     540
ATGATGGAGA  TGTCTACTTT  ATATATTGGA  ATAGAATATC  TATACCTAAC  ATACCATGTC     600
AAATTCAATT  AAGATAATAT  TGTCTTGTAT  GTTTCAGTGC  ATTGAGTCGA  CGAAGCCCTG     660
CTGCCGACTT  GAAGATCGCA  CATCGGTGCA  ATTTGGACGT  AAAGAGTACA  TCTGTGATCG     720
ATTCTTCGGC  GGACTCTGTG  CCCCATTAGA  CGTCATAAAC  AACCTTACAC  TGTATAAAGA     780
ATTGAGTGCA  CAATTGAACG  AAACTAATTT  GGCGGAACTC  TCCAATCTGT  ATTTCCAAGG     840
TATAAAGCAC  ACGCTGGGAA  TCAAGCCAGA  ACCCAAGATA  GAAGACGCGG  GAAAAGTCGA     900
```

-continued

| | | | | | |
|---|---|---|---|---|---|
| GGAAGTCGTG | AAACAGAGTA | CGGACAACAT | GAAATTGAGT | ACCGAAGCCG | AACGTGAACC | 960 |
| TGGAGACAAG | ACAGTATCCG | GAACAGAAAA | CTGGGTACAA | TCCCCAGACA | CGGATTCGCC | 1020 |
| TATTAACAAC | AAACCTGTAA | GTACATCATT | GTTAGCACTT | TGTCAACAAA | CCATTGGAGC | 1080 |
| ATATGCCTGG | CTGAAACTCT | TTACCGACGA | ATATGTCGTA | AGTGAGATGA | TGGAGATGCC | 1140 |
| TACTTTATAT | ATTGGAATAG | AATATCTATA | TCTAACATAC | CATGTCAAAT | TCAATTAAGA | 1200 |
| TAATATTGTC | TTGTATGTTT | CAGTGCATTG | AGTCGAAGGA | GTCCCGCTGC | CGACTTGAAA | 1260 |
| ATCGCACATT | GGTGCAATTT | GGACGTGAAG | AGGACATCTA | TGGTCGATTC | CTCGGCGGGA | 1320 |
| TCTATGCTCC | ATTAATAGTC | GTTAACAACT | CCACACTGTA | TTTAGAATTG | AGTAAAGGAA | 1380 |
| TGAACGAAAC | TAAATTGTCG | AATCTCAGCG | ATTGGTATAT | AGCAGCAGCT | GTAATCCCCA | 1440 |
| TGCCGGAATT | CAAGCCAGAA | TCCAAGATAG | AAGATGAGCG | AAAATCCCCA | GAAGCCCAG | 1500 |
| AACTCGAGTC | ACAGTGCATC | CCAAATTATG | AACTGGTAAG | TAATAATGG | ATACCACTTC | 1560 |
| ATTATTCAAT | CGTTCAAGCA | TATGACTGAT | GGAACTCCCC | AACAAAATGT | ATGTTTTATG | 1620 |
| CCACCACGCT | GAAACCCTCC | GAAGATGCTG | GCGACAGATG | CCTTTGACGA | TGAACGATTA | 1680 |
| CAGCATATAT | TGGAATAGGC | ATCGTGTACT | TTTCCACATG | TCACGCCCTT | TAACATGTAT | 1740 |
| TGAAGTAGAC | ATCGTCACGT | TTTATCTCTG | GGAGAGTCTG | TGAGCAATTT | CACGGGGTAC | 1800 |
| ACTCTTAGTT | ATTCTCAATC | TGTCGTCGTG | GATCTTGTGA | ACTTGAACTA | CATCAATGTC | 1860 |
| ATTTTGTATA | TTTTCAGTGC | GTGAATTCGA | AGAGGCCGTG | TTGCTGGGAG | AATAAGCTGT | 1920 |
| TCGCTGGTTC | ATCTAAACCC | CGTAATTTCG | TATGCGGTCT | ACACGGCCGA | AGCTACTGTT | 1980 |
| CACCATTCGA | TGGCTAACCA | ATTGGATATT | CGCTGGAAGG | TCGACAGGTT | AAGGGAACAA | 2040 |
| GAATCGATCA | AGAAGGAAGT | TTACGCTGTC | GACTTTTCAT | CAACAAGGAC | CACTTTTTCC | 2100 |
| GTTTTTCAAC | TGAGCTAGAG | GTGGTTCTTG | TTTTATACGA | ATATTTTTA | ATGTCTTTTG | 2160 |
| TGTTGCATTA | AGCATTTTTT | GAAATTTTGT | CTTTCCTTAT | ATCAATAATT | TTAGGTTGCA | 2220 |
| TGTCGTTGAA | AAACTATTTA | GTTTATTATA | AGAAGGAATA | ATGTAATATG | TTTCAAGATT | 2280 |
| TTTTTTCAAT | AAAGAGTAAT | GATAATTAAA | | | | 2310 |

( 2 ) INFORMATION FOR SEQ ID NO:2:

( i ) SEQUENCE CHARACTERISTICS:
        ( A ) LENGTH: 1472 base pairs
        ( B ) TYPE: nucleic acid
        ( C ) STRANDEDNESS: double
        ( D ) TOPOLOGY: unknown     ( i i ) MOLECULE TYPE: cDNA     ( i i i ) HYPOTHETICAL: NO     ( i x ) FEATURE:
        ( A ) NAME/KEY: CDS
        ( B ) LOCATION: 190..1155

( x i ) SEQUENCE DESCRIPTION: SEQ ID NO:2:

| | | | | | |
|---|---|---|---|---|---|
| GCTATCGCGA | TACAATTTCC | AGCTAAATTA | TCGTTAGGTC | GTCCGGGTCA | GCTCGAACGA | 60 |
| GAGGCCAGCT | ACTGGGTGCT | TACATGTATA | AAAGCACAGT | CCCGCCCTCA | ACAATCCAGA | 120 |
| GTATTACTTA | TCGCGGCCTG | CGCGTCGGAC | AATTTTTTCA | TTATAATAAA | TCATAGCATT | 180 |

ACCTGGACC ATG AAG TTT TTG TGG TTT GCA CTG GTC GCA GTG GTT ACA    228
         Met Lys Phe Leu Trp Phe Ala Leu Val Ala Val Val Thr
          1         5              10

GTG GCT GCG CAT CCT GTG GTC GAG ACA TCA ACT GAG AAA GAG GCC GAC    276
Val Ala Ala His Pro Val Val Glu Thr Ser Thr Glu Lys Glu Ala Asp
  15              20              25

-continued

```
GGG AAA ACT TCG CCC CAA TGC GAG CCA GGG TGC ATC GGC AAT TAC CAA       324
Gly Lys Thr Ser Pro Gln Cys Glu Pro Gly Cys Ile Gly Asn Tyr Gln
     30              35              40              45

CCT TGC ATT GAG TCG ACG AAG CCC TGC TGC CGA CTT GAA GAT CGC ACA       372
Pro Cys Ile Glu Ser Thr Lys Pro Cys Cys Arg Leu Glu Asp Arg Thr
                 50              55              60

TCG GTG CAA TTT GGA CGT AAA GAG TAC ATC TGT GAT CGA TTC TTC GGC       420
Ser Val Gln Phe Gly Arg Lys Glu Tyr Ile Cys Asp Arg Phe Phe Gly
             65              70              75

GGA CTC TGT GCC CCA TTA GAC GTC ATA AAC AAC CTT ACA CTG TAT AAA       468
Gly Leu Cys Ala Pro Leu Asp Val Ile Asn Asn Leu Thr Leu Tyr Lys
         80              85              90

GAA TTG AGT GCA CAA TTG AAC GAA ACT AAT TTG GCG GAA CTC TCC AAT       516
Glu Leu Ser Ala Gln Leu Asn Glu Thr Asn Leu Ala Glu Leu Ser Asn
     95             100             105

CTG TAT TTC CAA GGT ATA AAG CAC ACG CTG GGA ATC AAG CCA GAA CCC       564
Leu Tyr Phe Gln Gly Ile Lys His Thr Leu Gly Ile Lys Pro Glu Pro
110             115             120             125

AAG ATA GAA GAC GCG GGA AAA GTC GAG GAA GTC GTG AAA CAG AGT ACG       612
Lys Ile Glu Asp Ala Gly Lys Val Glu Glu Val Val Lys Gln Ser Thr
                130             135             140

GAC AAC ATG AAA TTG AGT ACC GAA GCC GAA CGT GAA CCT GGA GAC AAG       660
Asp Asn Met Lys Leu Ser Thr Glu Ala Glu Arg Glu Pro Gly Asp Lys
            145             150             155

ACA GTA TCC GGA ACA GAA AAC TGG GTA CAA TCC CCA GAC ACG GAT TCG       708
Thr Val Ser Gly Thr Glu Asn Trp Val Gln Ser Pro Asp Thr Asp Ser
        160             165             170

CCT ATT AAC AAC AAA CCT TGC ATT GAG TCG ACG GAG TCC CGC TGC CGA       756
Pro Ile Asn Asn Lys Pro Cys Ile Glu Ser Thr Glu Ser Arg Cys Arg
175             180             185

CTT GAA AAT CGC ACA TTG GTG CAA TTT GGA CGT GAA GAG GAC ATC TAT       804
Leu Glu Asn Arg Thr Leu Val Gln Phe Gly Arg Glu Glu Asp Ile Tyr
190             195             200             205

GGT CGA TTC CTC TTC TTT ATC TAT GCT CCA TTA ATA GTC GTT AAC AAC       852
Gly Arg Phe Leu Phe Phe Ile Tyr Ala Pro Leu Ile Val Val Asn Asn
                210             215             220

TCC ACA CTG TAT TTA GAA TTG AGT AAA GGA ATG AAC GAA ACT AAA TTG       900
Ser Thr Leu Tyr Leu Glu Leu Ser Lys Gly Met Asn Glu Thr Lys Leu
            225             230             235

TCG AAT CTC AGC GAT TGG TAT ATA GCA GCA GCT GTA ATC CCC ATG CCG       948
Ser Asn Leu Ser Asp Trp Tyr Ile Ala Ala Ala Val Ile Pro Met Pro
        240             245             250

GAA TTC AAG CCA GAA TCC AAG ATA GAA GAT GAG CGA AAA TCC CCA GAA       996
Glu Phe Lys Pro Glu Ser Lys Ile Glu Asp Glu Arg Lys Ser Pro Glu
255             260             265

GCC CCA GAA CTC GAG TCA CAG TGC ATC CCA AAT TAT GAA CTG TGC GTG      1044
Ala Pro Glu Leu Glu Ser Gln Cys Ile Pro Asn Tyr Glu Leu Cys Val
270             275             280             285

AAT TCG AAG AGG CCG TGT TGC TGG GAG AAT AAG CTG TTC GCT GGT TCA      1092
Asn Ser Lys Arg Pro Cys Cys Trp Glu Asn Lys Leu Phe Ala Gly Ser
                290             295             300

TCT AAA CCC CGT AAT TTC GTA TGC GGT CTA CAC GGC CGA AGC TAC TGT      1140
Ser Lys Pro Arg Asn Phe Val Cys Gly Leu His Gly Arg Ser Tyr Cys
            305             310             315

TCA CCA TTC GAT GGC TAACCAATTG GATATTCGCT GGAAGGTCGA CAGGTTAAGG      1195
Ser Pro Phe Asp Gly
        320

GAACAAGAAT CGATCAAGAA GGAAGTTTAC GCTGTCGACT TTTCATCAAC AAGGACCACT    1255

TTTTTCCGTT TTTCAACTGA GCTAGAGGTG GTTCTTGTTT TATACGAATA TTTTTTAATG    1315
```

```
TCTTTTGTGT  TGCATTAAGC  ATTTTTTGAA  ATTTTGTCTT  TCCTTATATC  AATAATTTTA      1 3 7 5

GGTTGCATGT  CGTTGAAAAA  CTATTTAGTT  TATTATAAGA  AGGAATAATG  TAATATGTTT      1 4 3 5

CAAGATTTTT  TTTCAATAAA  GAGTAATGAT  AATTAAA                                 1 4 7 2
```

( 2 ) INFORMATION FOR SEQ ID NO:3:

( i ) SEQUENCE CHARACTERISTICS:
    ( A ) LENGTH: 322 amino acids
    ( B ) TYPE: amino acid
    ( D ) TOPOLOGY: linear ( i i ) MOLECULE TYPE: protein ( x i ) SEQUENCE DESCRIPTION: SEQ ID NO:3:

```
Met  Lys  Phe  Leu  Trp  Phe  Ala  Leu  Val  Ala  Val  Val  Thr  Val  Ala  Ala
 1              5                        10                       15

His  Pro  Val  Val  Glu  Thr  Ser  Thr  Glu  Lys  Glu  Ala  Asp  Gly  Lys  Thr
               20                       25                       30

Ser  Pro  Gln  Cys  Glu  Pro  Gly  Cys  Ile  Gly  Asn  Tyr  Gln  Pro  Cys  Ile
               35                       40                       45

Glu  Ser  Thr  Lys  Pro  Cys  Cys  Arg  Leu  Glu  Asp  Arg  Thr  Ser  Val  Gln
      50                       55                       60

Phe  Gly  Arg  Lys  Glu  Tyr  Ile  Cys  Asp  Arg  Phe  Phe  Gly  Gly  Leu  Cys
 65                       70                       75                       80

Ala  Pro  Leu  Asp  Val  Ile  Asn  Asn  Leu  Thr  Leu  Tyr  Lys  Glu  Leu  Ser
                    85                       90                       95

Ala  Gln  Leu  Asn  Glu  Thr  Asn  Leu  Ala  Glu  Leu  Ser  Asn  Leu  Tyr  Phe
                   100                      105                      110

Gln  Gly  Ile  Lys  His  Thr  Leu  Gly  Ile  Lys  Pro  Glu  Pro  Lys  Ile  Glu
              115                      120                      125

Asp  Ala  Gly  Lys  Val  Glu  Glu  Val  Val  Lys  Gln  Ser  Thr  Asp  Asn  Met
         130                      135                      140

Lys  Leu  Ser  Thr  Glu  Ala  Glu  Arg  Glu  Pro  Gly  Asp  Lys  Thr  Val  Ser
145                      150                      155                      160

Gly  Thr  Glu  Asn  Trp  Val  Gln  Ser  Pro  Asp  Thr  Asp  Ser  Pro  Ile  Asn
                    165                      170                      175

Asn  Lys  Pro  Cys  Ile  Glu  Ser  Thr  Glu  Ser  Arg  Cys  Arg  Leu  Glu  Asn
               180                      185                      190

Arg  Thr  Leu  Val  Gln  Phe  Gly  Arg  Glu  Glu  Asp  Ile  Tyr  Gly  Arg  Phe
              195                      200                      205

Leu  Phe  Phe  Ile  Tyr  Ala  Pro  Leu  Ile  Val  Val  Asn  Asn  Ser  Thr  Leu
     210                      215                      220

Tyr  Leu  Glu  Leu  Ser  Lys  Gly  Met  Asn  Glu  Thr  Lys  Leu  Ser  Asn  Leu
225                      230                      235                      240

Ser  Asp  Trp  Tyr  Ile  Ala  Ala  Ala  Val  Ile  Pro  Met  Pro  Glu  Phe  Lys
                    245                      250                      255

Pro  Glu  Ser  Lys  Ile  Glu  Asp  Glu  Arg  Lys  Ser  Pro  Glu  Ala  Pro  Glu
               260                      265                      270

Leu  Glu  Ser  Gln  Cys  Ile  Pro  Asn  Tyr  Glu  Leu  Cys  Val  Asn  Ser  Lys
              275                      280                      285

Arg  Pro  Cys  Cys  Trp  Glu  Asn  Lys  Leu  Phe  Ala  Gly  Ser  Ser  Lys  Pro
     290                      295                      300

Arg  Asn  Phe  Val  Cys  Gly  Leu  His  Gly  Arg  Ser  Tyr  Cys  Ser  Pro  Phe
305                      310                      315                      320

Asp  Gly
```

( 2 ) INFORMATION FOR SEQ ID NO:4:

( i ) SEQUENCE CHARACTERISTICS:
        ( A ) LENGTH: 882 base pairs
        ( B ) TYPE: nucleic acid
        ( C ) STRANDEDNESS: double
        ( D ) TOPOLOGY: unknown     ( i i ) MOLECULE TYPE: cDNA     ( i i i ) HYPOTHETICAL: NO     ( i v ) ANTI-SENSE: NO     ( v i ) ORIGINAL SOURCE:
        ( A ) ORGANISM: Campoletis sonorensis virus     ( i x ) FEATURE:
        ( A ) NAME/KEY: CDS
        ( B ) LOCATION: 127..819

( x i ) SEQUENCE DESCRIPTION: SEQ ID NO:4:

```
GTCGAACTGT ATCTCTAACG ATCACAGTAG CTCAACCCAA ACTTTTCAAA ATTTTCGCAA          60

AAATCTGTTT TTTGGTGCTT ATGTGTTGCG TGTTCGTCTA TAAAAACATC AATTTGTAAA         120

CAATTG ATG TAC AAA TTT GTT TTG GTG ACG CTT CTG AGC TGT GTG CTG            168
       Met Tyr Lys Phe Val Leu Val Thr Leu Leu Ser Cys Val Leu
        1           5                  10              335

GCC CAA GCG AAT CCG CAG GTG TCG CGC CAT GGT CCC GCT GCT GTT GTA           216
Ala Gln Ala Asn Pro Gln Val Ser Arg His Gly Pro Ala Ala Val Val
 15              20                  25                       30

TCG GAT GCG AAT CGA ACG GTT CAT CCT CCA CCA GCT CAA AAC CAC GCC           264
Ser Asp Ala Asn Arg Thr Val His Pro Pro Pro Ala Gln Asn His Ala
                 35                  40                   45

GAG ATG GCA CGT TTC ATC GTT AAT CAA GCC GAC TGG GCA TCT CTG GCA           312
Glu Met Ala Arg Phe Ile Val Asn Gln Ala Asp Trp Ala Ser Leu Ala
             50                  55                  60

ACA ATC AGC ACT ATA GAA AAC ATC GCT TCT TAT CCA ATT GCC AGC ATA           360
Thr Ile Ser Thr Ile Glu Asn Ile Ala Ser Tyr Pro Ile Ala Ser Ile
         65                  70                  75

AAA TCA ATT AGT GAC GGA CCG GGC GGC AAT GGT ACC GGA GAT CCT TAT           408
Lys Ser Ile Ser Asp Gly Pro Gly Gly Asn Gly Thr Gly Asp Pro Tyr
 80                  85                  90

TTG TTT ATC TCA CCG AGG ACT TTC TCT GGT AGA GAC ATA GTT GCT GAT           456
Leu Phe Ile Ser Pro Arg Thr Phe Ser Gly Arg Asp Ile Val Ala Asp
 95              100                 105                     110

TCG CGA GCG AGT CTC GTC ATC TCC TTG GCT CAG GGT GCC TAC TGC AAG           504
Ser Arg Ala Ser Leu Val Ile Ser Leu Ala Gln Gly Ala Tyr Cys Lys
                 115                 120                 125

GAA AAT AAT TAT GAT CCA ATG GAC CCG CGA TGC GGA AGA GTT GTC ATC           552
Glu Asn Asn Tyr Asp Pro Met Asp Pro Arg Cys Gly Arg Val Val Ile
             130                 135                 140

ACC GGG CCG AGC CGA AAA AAT TGG GGA ATC CAG CCT CCG AAT ACC GCA           600
Thr Gly Pro Ser Arg Lys Asn Trp Gly Ile Gln Pro Pro Asn Thr Ala
         145                 150                 155

AGA GCC AGG ACT GCT TTC TTC GGA CGT CAT CCC GCG ATG NCC TAT ATG           648
Arg Ala Arg Thr Ala Phe Phe Gly Arg His Pro Ala Met Xaa Tyr Met
 160                 165                 170

CCT AGA GAT CAT GGT TTC TAC TTC GCG AAA ATA AAC ATT GAA AAT CTT           696
Pro Arg Asp His Gly Phe Tyr Phe Ala Lys Ile Asn Ile Glu Asn Leu
175                  180                 185                 190

CGT GTT CTT GCA TCA TTT GGT CCA TTC CAC GTG GTC TCC GCT CAA GAT           744
Arg Val Leu Ala Ser Phe Gly Pro Phe His Val Val Ser Ala Gln Asp
                 195                 200                 205
```

```
TAC  TAC  AGT  GCA  TCG  GTT  GGA  CAG  CGA  CAA  GAT  TGN  ATG  TAT  TCA  CTA      792
Tyr  Tyr  Ser  Ala  Ser  Val  Gly  Gln  Arg  Gln  Asp  Xaa  Met  Tyr  Ser  Leu
               210                      215                      220

TAT  ACG  AGT  GTA  CAA  ATT  GCA  CTT  CGG  TAATTTGAGA  AAGTTCAATC                 839
Tyr  Thr  Ser  Val  Gln  Ile  Ala  Leu  Arg
               225                      230

ATATTTGACT  CTCCGAGGAA  CNCGATACTG  TTGAAATAAA  ATC                                 882
```

(2) INFORMATION FOR SEQ ID NO:5:

(i) SEQUENCE CHARACTERISTICS:
        (A) LENGTH: 231 amino acids
        (B) TYPE: amino acid
        (D) TOPOLOGY: linear     (ii) MOLECULE TYPE: protein     (xi) SEQUENCE DESCRIPTION: SEQ ID NO:5:

```
Met  Tyr  Lys  Phe  Val  Leu  Val  Thr  Leu  Leu  Ser  Cys  Val  Leu  Ala  Gln
 1              5                        10                       15

Ala  Asn  Pro  Gln  Val  Ser  Arg  His  Gly  Pro  Ala  Ala  Val  Val  Ser  Asp
               20                       25                       30

Ala  Asn  Arg  Thr  Val  His  Pro  Pro  Pro  Ala  Gln  Asn  His  Ala  Glu  Met
               35                       40                       45

Ala  Arg  Phe  Ile  Val  Asn  Gln  Ala  Asp  Trp  Ala  Ser  Leu  Ala  Thr  Ile
      50                       55                       60

Ser  Thr  Ile  Glu  Asn  Ile  Ala  Ser  Tyr  Pro  Ile  Ala  Ser  Ile  Lys  Ser
 65                       70                       75                      80

Ile  Ser  Asp  Gly  Pro  Gly  Gly  Asn  Gly  Thr  Gly  Asp  Pro  Tyr  Leu  Phe
                    85                       90                       95

Ile  Ser  Pro  Arg  Thr  Phe  Ser  Gly  Arg  Asp  Ile  Val  Ala  Asp  Ser  Arg
               100                      105                      110

Ala  Ser  Leu  Val  Ile  Ser  Leu  Ala  Gln  Gly  Ala  Tyr  Cys  Lys  Glu  Asn
               115                      120                      125

Asn  Tyr  Asp  Pro  Met  Asp  Pro  Arg  Cys  Gly  Arg  Val  Val  Ile  Thr  Gly
     130                      135                      140

Pro  Ser  Arg  Lys  Asn  Trp  Gly  Ile  Gln  Pro  Pro  Asn  Thr  Ala  Arg  Ala
145                      150                      155                      160

Arg  Thr  Ala  Phe  Phe  Gly  Arg  His  Pro  Ala  Met  Xaa  Tyr  Met  Pro  Arg
                    165                      170                      175

Asp  His  Gly  Phe  Tyr  Phe  Ala  Lys  Ile  Asn  Ile  Glu  Asn  Leu  Arg  Val
                    180                      185                      190

Leu  Ala  Ser  Phe  Gly  Pro  Phe  His  Val  Val  Ser  Ala  Gln  Asp  Tyr  Tyr
               195                      200                      205

Ser  Ala  Ser  Val  Gly  Gln  Arg  Gln  Asp  Xaa  Met  Tyr  Ser  Leu  Tyr  Thr
     210                      215                      220

Ser  Val  Gln  Ile  Ala  Leu  Arg
225                      230
```

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:6:

GGTGGCGACG ACTCCTGGAG C                                                                                  21

(2) INFORMATION FOR SEQ ID NO:7:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "PRIMER"

(iii) HYPOTHETICAL: NO (xi) SEQUENCE DESCRIPTION: SEQ ID NO:7:

GACACCAACT GGTAATG                                                                                       17

(2) INFORMATION FOR SEQ ID NO:8:

(i) SEQUENCE CHARACTERISTICS:
                (A) LENGTH: 26 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "PRIMER"

(iii) HYPOTHETICAL: NO (xi) SEQUENCE DESCRIPTION: SEQ ID NO:8:

GCACTTAACT TTTTTTTTT TTTTT                                                                               26